(12) United States Patent
Holden et al.

(10) Patent No.: US 7,372,565 B1
(45) Date of Patent: May 13, 2008

(54) SPECTROMETER MEASUREMENT OF DIFFRACTING STRUCTURES

(75) Inventors: James M. Holden, San Jose, CA (US); William A. McGahan, Spicewood, TX (US); Richard A. Yarussi, San Francisco, CA (US); Pablo I. Rovira, San Francisco, CA (US); Roger R. Lowe-Webb, Mountain View, CA (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

(21) Appl. No.: 11/540,990

(22) Filed: Sep. 28, 2006

Related U.S. Application Data

(63) Continuation of application No. 09/670,000, filed on Sep. 25, 2000, now Pat. No. 7,115,858.

(51) Int. Cl.
*G01J 3/28* (2006.01)
(52) U.S. Cl. .................................... 356/327
(58) Field of Classification Search ............... None
See application file for complete search history.

(56) References Cited

U.S. PATENT DOCUMENTS

| | | | |
|---|---|---|---|
| 4,141,780 A | 2/1979 | Kleinknecht et al. | 156/626 |
| 4,172,664 A | 10/1979 | Charsky et al. | 356/356 |
| 4,408,884 A | 10/1983 | Kleinknecht et al. | 356/355 |
| 4,555,767 A | 11/1985 | Case et al. | 364/563 |
| 4,582,389 A | 4/1986 | Wood et al. | 359/14 |
| 4,593,368 A | 6/1986 | Fridge et al. | 364/525 |
| 4,672,196 A | 6/1987 | Canino | 250/225 |
| 4,707,610 A | 11/1987 | Lindow et al. | 250/560 |
| 4,748,335 A | 5/1988 | Lindow et al. | 250/559.22 |
| 5,007,708 A | 4/1991 | Gaylord et al. | 359/569 |
| 5,035,770 A | 7/1991 | Braun | 156/643 |
| 5,042,949 A | 8/1991 | Greenberg et al. | 356/345 |
| 5,042,951 A | 8/1991 | Gold et al. | 356/369 |
| 5,045,704 A | 9/1991 | Coates | 250/372 |
| 5,164,790 A | 11/1992 | McNeil et al. | 356/355 |

(Continued)

FOREIGN PATENT DOCUMENTS

| | | |
|---|---|---|
| EP | 0 402 191 A1 | 12/1990 |
| EP | 0 402 191 B1 | 12/1990 |
| EP | 0 601 580 A1 | 6/1994 |
| EP | 1 037 012 A1 | 9/2000 |
| JP | 59-0225038 | 12/1984 |

(Continued)

OTHER PUBLICATIONS

Prosecution History of U.S. Appl. No. 09/670,000 filed Sep. 25, 2000, by Holden et al.

(Continued)

*Primary Examiner*—Tu T Nguyen
(74) *Attorney, Agent, or Firm*—Silicon Valley Patent Group LLP

(57) ABSTRACT

A normal incidence reflectometer includes a rotatable analyzer/polarizer for measurement of a diffracting structure. Relative rotation of the analyzer/polarizer with respect to the diffracting structure permits analysis of the diffracted radiation at multiple polarity orientations. A spectograph detects the intensity of the spectral components at different polarity orientations. Because the normal incidence reflectometer uses normally incident radiation and an analyzer/polarizer that rotates relative to the diffracting structure, or vice-versa, the orientation of the diffracting structure does not affect the accuracy of the measurement. Thus, the sample holding stage may use X, Y, and Z, as well as r-θ type movement and there is no requirement that the polarization orientation of the incident light be aligned with the grating of the diffraction structure. A non-linear multivariate regression process is used to adjust the parameters of an optical model, such as rigorous coupled-wave analysis, to provide a match with the measured data.

24 Claims, 4 Drawing Sheets

U.S. PATENT DOCUMENTS

| | | | |
|---|---|---|---|
| 5,191,216 A | 3/1993 | Henderson et al. | 257/28 |
| 5,216,680 A | 6/1993 | Magnusson et al. | 372/20 |
| 5,337,146 A | 8/1994 | Azzam | 356/367 |
| 5,349,440 A | 9/1994 | DeGroot | 356/349 |
| RE34,783 E | 11/1994 | Coates | 250/372 |
| 5,363,171 A | 11/1994 | Mack | 355/68 |
| 5,519,493 A | 5/1996 | Reiley | 356/367 |
| 5,555,474 A | 9/1996 | Ledger | 356/381 |
| 5,596,406 A * | 1/1997 | Rosencwaig et al. | 356/327 |
| 5,607,800 A | 3/1997 | Ziger | 430/8 |
| 5,739,909 A | 4/1998 | Blayo et al. | 356/369 |
| 5,747,813 A | 5/1998 | Norton et al. | 250/372 |
| 5,841,139 A | 11/1998 | Sostek et al. | 250/339.12 |
| 5,867,276 A | 2/1999 | McNeil et al. | 356/445 |
| 5,880,838 A | 3/1999 | Marx et al. | 356/498 |
| 5,889,593 A | 3/1999 | Bareket | 356/445 |
| 5,900,633 A | 5/1999 | Solomon et al. | 250/339.08 |
| 5,956,145 A | 9/1999 | Green et al. | 356/364 |
| 5,963,329 A | 10/1999 | Conrad et al. | 356/613 |
| 6,031,614 A | 2/2000 | Michaelis et al. | 356/369 |
| 6,097,488 A | 8/2000 | Grek et al. | 356/364 |
| 6,100,985 A | 8/2000 | Scheiner et al. | 356/630 |
| 6,281,974 B1 | 8/2001 | Scheiner et al. | 356/381 |
| 6,366,861 B1 | 4/2002 | Waldhauer et al. | 702/35 |
| 6,368,881 B1 | 4/2002 | Brouillette et al. | 438/7 |
| 6,429,930 B1 | 8/2002 | Littau et al. | 356/124 |
| 6,429,943 B1 | 8/2002 | Opsal et al. | 356/625 |
| 6,476,920 B1 | 11/2002 | Scheiner et al. | 356/630 |
| 6,483,580 B1 * | 11/2002 | Xu et al. | 356/300 |
| 6,556,947 B1 | 4/2003 | Scheiner et al. | 702/172 |
| 6,657,736 B1 | 12/2003 | Finarov et al. | 356/625 |
| 6,673,637 B2 | 1/2004 | Wack et al. | 438/14 |
| 6,690,469 B1 | 2/2004 | Shibata et al. | 356/369 |
| 7,115,858 B1 | 10/2006 | Holden et al. | 356/369 |
| 2002/0018217 A1 | 2/2002 | Weber-Grabau et al. | 356/601 |
| 2002/0024669 A1 | 2/2002 | Danner et al. | 356/369 |
| 2002/0033945 A1 | 3/2002 | Xu et al. | 356/369 |
| 2002/0033954 A1 | 3/2002 | Niu et al. | 356/601 |
| 2002/0035455 A1 | 3/2002 | Niu et al. | 703/4 |
| 2002/0038196 A1 | 3/2002 | Johnson et al. | 702/179 |
| 2002/0051564 A1 | 5/2002 | Benesh et al. | 382/145 |

FOREIGN PATENT DOCUMENTS

| | | |
|---|---|---|
| JP | 11-211421 | 8/1999 |
| JP | 11-211422 | 8/1999 |
| SU | 1747877 A1 | 7/1992 |
| WO | WO 99/45340 A1 | 9/1999 |
| WO | WO 02/25723 A2 | 3/2002 |
| WO | WO 02/27288 A1 | 4/2002 |
| WO | WO 02/50501 A1 | 6/2002 |
| WO | WO 02/079760 A2 | 10/2002 |

OTHER PUBLICATIONS

Prosecution History of U.S. Appl. No. 10/085,832 filed Feb. 27, 2002, by Holden et al., now abandoned.

"A Diffraction Grating Analysis Tool", downloaded May 7, 2001 from <http://www.gsolver.com/gsprod.html>, Grating Solve Development Co. (1999).

Ahmed, S., et al. "Comparison of beam propagation method and rigorous coupled-wave analysis for single and multiplexed volume gratings", Applied Optics, vol. 35, No. 22, Aug. 1, 1996, pp. 4426-4435.

Azzam, R. et al., "Ellipsometry And Polarized Light" Elsevier Science Publishers (1977, 1987) pp. 476-481.

Bao, G. et al., "Mathematical studies in rigorous grating theory", J. Opt. Soc. Am. A, vol. 12, No. 5 (1995), pp. 1029-1042.

Bao, G. et al., "Modeling and Optimal Design of Diffractive Optical Structures", pp. 1-27. (The correct site is Survey on Industrial Math. 8 (1998), 37-62).

Benson, T. et al., "In-situ Spectroscopic Reflectometry for Polycrystalline Silicon Thin Film Etch Rate Determination During Reactive Ion Etching", Dept. of Electrical Engineering & Computer Science an the Center for Display Technology & Manfuacturing, University of Michigan, pp. 1-34.

Bischoff J. et al., "Modeling of optical scatterometry with finite-number-of periods gratings", SPIE vol. 3743 (1999) pp. 41-46.

Bischoff, J. et al., "Single feature metrology by means of light scatter analysis", SPIE vol. 3050 (1997) pp. 574-589.

Bishop, K. P. et al., "Gratings line shape characterization using scatterometry", SPIE, vol. 1545 (1991) pp. 64-73.

Bishop, K. P. et al., "Use of scatterometry for resist process control", Proc. SPIE—Int. Soc. Opt. Eng., vol. 1673 (1992) pp. 441-452.

Bosenberg, W. et al., "Linewidth Measurement on IC Wafers by Diffraction from Grating Test Patterns", Solid State Technology, vol. 26, No. 7 (1983) pp. 79-85.

Brauer, R. et al., "Eletromagnetic diffraction analysis of two-dimensional gratings", Optics Communications, vol. 100 (1993) pp. 1-5.

Chateau, N. et al., "Algorithm for the rigorous coupled-wave analysis of grating diffraction," J. Opt. Soc. Am. A, vol. 11 (1994), pp. 1321-1331.

Corle, T., et al., "Polarization-enhanced imaging of photoresist gratings in the real-time scanning optical microscope", Applied Optics, vol. 33, No. 4 (1994) pp. 670-677.

Coulombe, S. A. et al., "Modal characteristics of short-pitch photoresist gratings exhibiting zero-order diffraction anomalies", J. Opt. Soc. Am. A, vol. 16, No. 12 (Dec. 1999), pp. 2904-2913.

Coulombe, S. A. et al., "Scatterometry measurement of sub-0.1 μm linewidth gratings", J. Vac. Sci. Technol.. B, vol. 16, No. 1 (1998) pp. 80-87.

Coulombe, S. et al., "Ellipsometric-Scatterometry for sub-01. mm CD measurements" SPIE vol. 3332 (1988) pp. 282-292.

Damar, H. et al., "Diffraction Characterization for Process Monitoring, Linewidth Measurement and Alignment" SPIE vol. 470 (1984) pp. 157-163.

Davidson, M. et al., "A comparison between rigorous light scattering methods", SPIE vol. 3051 (1997) pp. 606-619.

Dong Hoon Lee, et al., "Analysis of topological efffects of phase-shifting mask by boundary element method", J. Inst. Electron. Eng. Korea D (South Korea), vol. 36-D, No. 11, Nov. 1999, pp. 33-44.

Galarza, C. et al., "Real-time Estimation of Patterned Wafer Parameters Using In Situ Spectroscopic Ellipsometry", Proceedings of the IEEE (1999) pp. 773-778.

Gaspar, S. M. et al., "Laser scatterometry for process characterization", AIP Conference Proceedings, vol. 227, No. 1, (1991) pp. 54-55.

Gaylord, T. et al., "Analysis and Applications of Optical Diffraction by Gratings," Proceedings of the IEEE, vol. 73, (1984), pp. 894-937 (1985).

Glytsis, E. et al., "Rigorous Coupled-Wave Analysis And Applications Of Grating Diffraction", Critical Reviews Of Optical Science and Technology, vol. CR49 (1993), pp. 1-31.

Glytsis, E. et al., "Three-dimensional (vector) rigorous coupled-wave analysis of anisotropic grating diffraction", J. Opt. Soc. Am. A, vol. 7, No. 8 (1990), pp. 1399-1420.

Glytsis, E. N. et al., "Review of rigorous coupled-wave analysis and of homogeneous effective medium approximations for high spatial-frequency surface-relief", In NASA. Marshall Space Flight Center, Conference on Binary Optics: An Opportunity for Technical Exchange Feb. 23-25, 1993, p. 61-76.

Han, Chang-Wook, et al., "Rigorous coupled-wave analysis of antireflective surface-relief gratings", J. Opt. Soc. Korea (South Korea) vol. 1, No. 1, Mar. 1997, pp. 26-35.

Han, S. et al., "Electromagnetic scattering of two-dimensional surface-relief dielectric grating", Applied Optics, vol. 31 (1992) pp. 2343-2352.

Hatab, Ziad R. et al., "Sixteen-megabit dynamic random access memory trench depth characterization using two-dimensional diffraction analysis", J. Vac. Sci. Technol. B, vol. 13, No. 2 (1995) pp. 174-182.

Hauge, P., "Recent Developments in Instrumentation in Ellipsometry", Surface Science 96, (1980) pp. 108-140.

Haverlag, M. et al., "In situ ellipsometry and reflectometry during etching of patterned surfaces: Experiments and simulations", *Journal of Vacuum Science & Technology B*, vol. 10, No. 6 (1992) pp. 2412-2418.

Heimann, P. et al., "Optical Etch-Rate Monitoring: Computer Simulation of Reflectance", *Journal Electrochem. Soc.*, vol. 131, No. 4 (1984) pp. 881-885.

Henderson, G. N., "Semiconductor quantum electron wave transport, diffraction, and interference: analysis, device, and measurement", Dissertation Georgia Institute Of Technology, vol. 54-10B, 1993, pp. 5312 209 page(s).

Hickman, K. C. et al., "Use of diffracted light from latent images to improve lithography control", *J. Vac. Sci. & Tech. B*, vol. 10, No. 5 (1992) pp. 2259-2266.

Huang, H. et al., "Normal-incidence spectroscopic ellipsometry for critical dimension monitoring", *Applied Physics Letters*, vol. 78 (2001) pp. 3983-3985.

Jarem, J. M., et al., "Rigorous coupled-wave analysis of photorefractive reflection gratings", J. Opt. Soc. Am. B, Opt. Phys. (USA) vol. 15, No. 7, Jul. 1998, pp. 2099-2106.

Jarem, J.M. "A rigorous coupled-wave analysis and crossed-diffraction grating analysis of radiation and scattering from three-dimensional inhomogeneous objects" IEEE Transactions on Antennas and Propagation, vol. 46, No. 5, May 1998, p. 740, 741.

Jiang Yongyuan, et al., Rigorous coupled wave analysis of dynamic diffraction properties of photorefractive phase grating Acta Photonica Sin. (China) vol. 29, No. 3, Mar. 2000, pp. 216-222.

Jiang Yongyuan, et al., "Rigorous coupled wave analysis of dynamic property of photorefractive anisotropic self-diffraction" Acta Photonica Sin. (China), vol. 29, No. 9, Sep. 2000, pp. 787-790.

Kamiya, N., "Rigorous coupled-wave analysis for practical planar dielectric gratings. 2. Diffraction by a surface-eroded hologram layer" Appl. Opt. (USA) vol. 37, No. 25, Sep. 1, 1998, pp. 5854-5863.

Kamiya, N., "Rigorous coupled-wave analysis for practical planar dielectric gratings. 3. Increase of higher-order lights owing to degenerated complex diffraction" Appl. Opt. (USA), vol. 37, No. 25, Sep. 1, 1998, pp. 5864-5878.

Kamiya, N., "Rigorous coupled-wave analysis for practical planar dielectric gratings. I. Thickness-changed holograms and some characteristics of diffraction efficiency", Appl. Opt. (USA) vol. 37, No. 25, Sep. 1, 1998, pp. 5843-5853.

Kleinknecht, H. et al., "Linewidth measurement on IC masks and wafers by grating test patterns", *Applied Optics*, vol. 19, No. 4 (1980) pp. 525-533.

Kong, W. et al., "A Hybrid Analysis Ellipsometry Data from Patterned Structures" *Characterization and Metrology for ULSI Technology: 2000 International Conference*, pp. 373-377 (2001).

Kong, W. et al., "Analysis of Time-Evolved Spectroscopic Ellipsometry Data from Patterned Structures for Etching Process Monitoring and Control", Dept. of Electrical Engineering and Computer Science, University of Michigan, Four pages.

Giapis, K. et al., "Use of Light Scattering in Characterizing Reactively Ion Etched Profiles", J. Vac. Sci. Technol. A, vol. 9 (1981), pp. 664-668.

Krukar, R. et al., Overlay and Grating Line Shape Metrology Using Optical Scatterometry (unclassifed) DARPA I 1993 Final Report, (Oct. 11, 1993) Thirty-six pages.

Krukar, R. et al., "Reactive ion etching profile and depth characterization using statistical and neural network analysis of light scattering data", *J. Appl. Phys.*, vol. 74, No. 6 (1993) pp. 3698-3706.

Krukar, R. H. et al., "Analyzing simulated and measured optical scatter for semiconductor process verification", *Proc. SPIE—Int. Soc. Opt. Eng.*, vol. 1907 (1993) pp. 238-249.

Krukar, R. H. et al., "Using scattered light modeling for semiconductor critical dimension metrology and calibration", *Proc. SPIE—Int. Soc. Opt. Eng.*, vol. 1926 (1993) pp. 60-71.

Krukar, R. H. et al., "Wafer examination and critical dimension estimation using scattered light" *Proc. SPIE—Int. Soc. Opt. Eng.*, vol. 1661 (1992) pp. 323-332.

Lee, M. et al., "Analysis of Reflectometry and Ellipsometry Data from Patterned Structures", *Characterization and Metrology for ULSI Technology*, (1998) pp. 331-334.

Lee, S. G., et al., "More stable algorithm for rigorous coupled wave analysis applied to topography simulation in optical lithography and its numerical implementation", Proc. SPIE—Int. Soc. Opt. Eng. (USA), vol. 2726, 1996, pp. 288-298.

Lochbihler, H. et al., "Characterization of highly conducting wire gratings using an electromagnetic theory of diffraction" *Optics Communications* 100 (1993) pp. 231-239.

Lochbihler, H. et al., "Characterization of x-ray transmission gratings" *Applied Optics*, vol. 31 (1992) pp. 964-971.

Logofatu, P. C. et al. "Identity of the cross-reflection coefficients for symmetric surface-relief gratings", *J. Opt. Soc. Am. A, Opt.* vol. 16 No. 5 (May 1999) pp. 1108-1114.

Logofatu, P. C. et al., "Sensitivity analysis of fitting for scatterometry", *Proc. SPIE—Int. Soc. Opt. Eng.*, vol. 3677 (1999) pp. 177-183.

Logofatu, P.C., "Sensitivity-optimized scatterometry", Dissertation The University of New Mexico, vol. 61-11B, 2000, pp. 5942 181 page(s).

Lopez, A. G. "Reformulation of the rigorous coupled-wave analysis (RCWA) equations: Photonic crystals applications" Dissertation, Cornell University, vol. 61-04B, 2000, pp. 2113 136 pages.

Marx, D. et al., "Polarization quadrature measurement of subwavelength diffracting structures", *Applied Optics*, vol. 36, No. 25 (1997), pp. 6434-6440.

McNeil, J. R. "Application of optical scatterometry to microelectronics processing", *Technical Digest. Summaries of Papers Presented at the Conference on Lasers and Electro-Optics.*, vol. 6 (1998) pp. 348-349.

McNeil, J. R. et al., "Scatterometry applied to microelectronics processing", *Solid State Technol.*, vol. 36, No. 3 (1993) pp. 29-30.

McNeil, J. R., et al., "Scatterometry applied to microelectronics processing" *Solid State Technol.* vol. 36, No. 4 (1993) pp. 53-56.

McNeil, J. R., "Instrumentation to Enhance Optical Scatterometry for Semiconductor Metrology Development", Final Rept. Sep. 1, 1993-Feb. 28, 1998, Contract No. F49620-93-1-0512, Defense Technical Information Center (DTIC) order No. AD-A354-189 (1998) (23 pages).

McNeill, J. et al., "Scatterometry Applied to Microelectronics Processing" Microlithography World (1992) pp. 16-22.

Mills, D. et al., "Spectral ellipsometry on patterned wafers," SPIE, vol. 2637 (1995) pp. 194-203.

Milner, L. M et a., "Latent image exposure monitor using scatterometry", SPIE Proceedings, vol. 1673 (1992), 10 pages.

Milner, L. M. et al., "Lithography process monitor using light diffracted from a latent image", Proc. SPIE—Int. Soc. Opt. Eng., vol. 1926 (1993) pp. 94-105.

Minhas, B. K. et al., "Ellipsometric scatterometry for the metrology of sub-0.1—µm-linewidth structures", Applied Optics, vol. 37 No. 22 (Aug. 1998) pp. 5112-5115.

Minhas, B. K. et al., "Towards sub-0.1 mu m CD measurements using scatterometry", Proc. SPIE—Int. Soc. Opt. Eng., vol. 2725 (1996) pp. 729-739.

Moharam, M. et al., "Diffraction analysis of dielectric surface-relief gratings", J. Opt. Soc. Am., vol. 72 (1982) pp. 1385-1392.

Moharam, M. et al., "Diffraction characteristics of photoresist surface-relief gratings" Applied Optics, vol. 23 (1984) pp. 3214-3220.

Moharam, M. et al., "Formulation for stable and efficient implementation of the rigorous coupled-wave analysis of binary gratings", J. Opt. Soc. Am., vol. 12 (1995) pp. 1068-1076.

Moharam, M. et al., "Rigorous coupled-wave analysis of planar-grating diffraction", J. Opt. Soc. Am., vol. 71, No. 7 (1981) pp. 811-818.

Moharam, M. et al., "Stable implementation of the rigorous coupled-wave analysis for surface-relief gratings: enhanced transmittance matrix approach", J. Opt. Soc Am., vol. 12 (1995) pp. 1077-1086.

Moharam, M. et al., "Three-dimensional vector coupled-wave analysis of planar-grating diffraction", *J. Opt. Soc. Am.*, vol. 73, No. 9 (1983), pp. 1105-1112.

Moharam, M., "Coupled-Wave Analysis of Two-Dimensional Dielectric Gratings", *SPIE* vol. 883 (1988) pp. 8-11.

Moharam, M.G. et.al, "Rigorous Coupled-Wave Analysis of Grating Diffraction- E-mode polarization and losses", Journal of the Optical Society of America, vol. 73, No. 4, Apr. 1983, p. 451-455.

Moharam, M.G. et.al, "Rigorous coupled-wave analysis of metallic surface-relief gratings" Optical Society of America, Journal, A: Optics and Image Science Optical Society of America, Journal, A: Optics and Image Science Optical Society of America, Journal, A: Optics and Image Science, vol. 3, Nov. 1986, p. 1780-1787.

Motulsky, Harvey Analyzing Data with GraphPad Prism, 1999, pp. 1, 2, and 157-170.

Murnane, M. R. et al., "Scatterometry for 0.24-0.70 um developed photoresist metrology", *SPIE*, vol. 2439 (1995) pp. 427-436.

Murname, M. R. et al., "Subwavelength photoresist grating metrology using scatterometry", *Proc. SPIE—Int. Soc. Opt. Eng.*, vol. 2532 (1995) pp. 251-261.

Nakagawa, W., et al., "Analysis of near field effects in artificial dielectric structures using rigorous coupled-wave analysis", Conference Proceedings -Lasers and Electo-Optics Society Annual Meeting-LEOS, vol. 2, 1999, p. 495-496.

Naqvi, S. "A simple technique for linewidth measurement of gratings on photomasks", *Proc. SPIE—Int. Soc. Opt. Eng.*, vol. 1261 (1990) pp. 495-504.

Naqvi, S. et al. "Grating parameter estimation using scatterometry" *Proc. SPIE—Int.Soc. Opt. Eng.*, vol. 1992 (1993) pp. 170-180.

Naqvi, S. et al., "Diffractive techniques for lithographic process monitorng and control", *J. Vac. Sci. Technol. B*, vol. 12, No. 6 (1994) pp. 3600-3606.

Naqvi, S. et al., "Linewidth measurement of gratings on photomasks: a simple technique", *Applied Optics*, vol. 31, No. 10 (1992) pp. 1377-1384.

Naqvi, S. S. H., et al., "Optical scatterometry for process metrology", *Optical metrology; Proceedings of the Conference*, (Jul. 1999) pp. 129-144.

Naqvi, S. et al., "Scatterometry and the Simulation of Diffraction-Based Metrology" *Microlithography World* (1993) pp. 5-14.

Naqvi, S. et al., "Etch depth estimation of large-period silicon gratings with multivariate calibration of rigorously simulated diffraction profiles," *J. Opt. Soc. Am. A.*, vol. 11, No. 9 (1984), pp. 2485-2493.

Peng, Song, et al., "Efficient and stable implementation of rigorous coupled-wave analysis for surface-relief gratings", Proc. SPIE—Int. Soc. Opt. Eng. (USA), vol. 2532, 1995, pp. 475-480.

Peng, Song, et al., "Efficient implementation of rigorous coupled-wave analysis for surface-relief gratings", Journal of the Optical Society of America A: Optics and Image Science, and Vision, vol. 12, No. 5, May 1995, p. 1087-1096.

Press, W. et al., "Numerical Recipes: The Art of Scientific Computing,", *Cambridge University Press*, Section 14.4 (1986), pp. 521-528.

Prins, S.L. et al., "Scatterometric sensor for PEB process control", *Proc. SPIE—Int. Soc. Opt. Eng.*, vol. 2725 (1996) pp. 710-719.

Raymond, C. et al., "Metrology of subwavelength photoresist gratings using optical scatterometry" *J. Vac. Sci. Technology. B* 13 (1995) pp. 1484-1495.

Raymond, C. et al., "Resist and etched line profile characterization using scatterometry" *SPIE* vol. 3050 (1977) 476-486.

Raymond, C. et al., "Scatterometry for the measurement of mental features" *Proceedings of SPIE* vol. 2998 (2000) pp. 135-146.

Raymond, C. J. et al., "Multiparameter CD measurement using scatterometry", *Proc. SPIE—Int. Soc. Opt. Eng.*, vol. 2725 (1996) pp. 698-709.

Raymond, C. J. et al., "Multiparameter grating metrology using optical scatterometry" *J. of Vac. Sci. Tech. B*, vol. 15, No. 2 (1997) pp. 361-368.

Raymond, C. J. et al., "Multi-parameter process metrology using scatterometry", *Proc. SPIE—Int. Soc. Opt. Eng.*, vol. 2638 (1995) pp. 84-93.

Raymond, C. J. et al., "Resist and Etched line profile characterization using scatterometry", *Proc. SPIE—Int. Soc. Opt. Eng.*, vol. 3050 (1997) pp. 476-486.

Raymond, C. J. et al., "Scatterometry for CD measurement of etched structures", *Proc. SPIE—Int. Soc. Opt. Eng.*, vol. 2725 (1996) pp. 720-728.

Stover, J. C., et al., "Modeled and measured scatter from vias", SPIE Conf on Surface Characterization of Computer Disks, Wafers, and Flat Panel Displays, Jan. 1999, pp. 65-71.

Sun, J. et al., "Profile Measurement on IC Wafers by Holographic Interference", *SPIE* vol. 673 (1986) pp. 135-143.

Tadros, K., "Understanding metrology of polysilicon gates through reflectance measurements and simulation", *SPIE* vol. 1464 (1991) pp. 177-186.

Tu, K. et al., "Multiple-scattering theory of wave diffraction by superposed volume gratings", *J. Opt. Soc. Am. A.*, vol. 7, No. 8 (1990), pp. 1421-1435.

Wilson, S. M. G. et al., "Phase shift mask metrology using scatterometry", *Proc. SPIE—Int. Soc. Opt. Eng.*, vol. 2322 (1994) pp. 305-315.

Ziger, D. et al., "Linesize effects on ultraviolet reflectance spectra", *Society of Photo-Optical Instrumentation Engineers* (1997), Paper 37046.

Zylberberg, Z. et al., "Rigorous coupled-wave analysis of pure reflection gratings" Optical Society of America, Journal, vol. 73, Mar. 1983, p. 392-398.

Non-Final Office Action mailed on Mar. 14, 2002 for U.S. Appl. No. 09/670,000, eleven pages.

Response to Non-Final Office Action mailed on Jun. 13, 2002 for U.S. Appl. No. 09/670,000, twenty-two pages.

Non-Final Office Action mailed on Sep. 13, 2002 for U.S. Appl. No. 09/670,000, ten pages.

Response to Non-Final Office Action mailed on Jan. 10, 2003 for U.S. Appl. No. 09/670,000, nineteen pages.

Non-Final Office Action mailed on Mar. 17, 2004 for U.S. Appl. No. 09/670,000, eleven pages.

Response to Non-Final Office Action mailed on Jun. 16, 2004 for U.S. Appl. No. 09/670,000, thirteen pages.

Non-Final Office Action mailed on Jul. 27, 2004 for U.S. Appl. No. 09/670,000, eleven pages.

Response to Non-Final Office Action mailed Jul. 22, 2005 for U.S. Appl. No. 09/670,000, nine pages.

Final Office Action mailed on Oct. 14, 2005 for U.S. Appl. No. 09/670,000, eleven pages.

Response to Final Office Action with Request for Continued Examination mailed on Apr. 7, 2006 for U.S. Appl. No. 09/670,000, ten pages.

Notice of Allowance mailed on Jun. 16, 2006 for U.S. Appl. No. 09/670,000, five pages.

Preliminary Amendment mailed on Feb. 27, 2002 for U.S. Appl. No. 10/085,832, one page.

Non-Final Office Action mailed on Jun. 17, 2002 for U.S. Appl. No. 10/085,832, seven pages.

Response to Non-Final Office Action mailed on Sep. 17, 2002 for U.S. Appl. No. 10/085,832, seventeen pages.

Final Office Action mailed on Dec. 4, 2002 for U.S. Appl. No. 10/085,832, eight pages.

Response to Final Office Action with Request for Continued Examination mailed on Mar. 4, 2003 for U.S. Appl. No. 10/085,832, fourteen pages.

Non-Final Office Action mailed on Jun. 4, 2003 for U.S. Appl. No. 10/085,832, eight pages.

Response to Non-Final Office Action mailed on Sep. 4, 2003 for U.S. Appl. No. 10/085,832, fourteen pages.

Final Office Action mailed on Feb. 25, 2004 for U.S. Appl. No. 10/085,832, eleven pages.

Response to Final Office Action with Request for Continued Examination mailed on May 25, 2004 for U.S. Appl. No. 10/085,832, twelve pages.

Preliminary Amendment mailed on Jun. 9, 2004 for U.S. Appl. No. 10/085,832, eleven pages.

Non-Final Office Action mailed on Nov. 16, 2004 for U.S. Appl. No. 10/085,832, eleven pages.

Response to Non-Fianl Office Action mailed on Feb. 15, 2005 for U.S. Appl. No. 10/085,832, twelve pages.

Final Office Action mailed on May 10, 2005 for U.S. Appl. No. 10/085,832, twelve pages.

* cited by examiner

SPECTROMETER MEASUREMENT OF DIFFRACTING STRUCTURES

CROSS REFERENCE TO RELATED APPLICATION

This application is a continuation of and claims priority to U.S. patent application Ser. No. 09/670,000, filed Sep. 25, 2000, entitled "Apparatus and Method for the Measurement of Diffracting Structures", which is incorporated herein by reference.

FIELD OF THE INVENTION

This invention relates in general to metrology devices and in particular to metrology devices that may be used to measure diffracting structures.

BACKGROUND

It is desirable to measure circuit structures and other types of structures, e.g., resist structures, during the production of integrated circuits. Optical metrology tools are particularly well suited for measuring microelectronic structures because they are nondestructive, accurate, repeatable, fast, and inexpensive. Often different metrology tools are required to measure different structures or parameters on a wafer. For example, certain structures on a wafer act as diffraction gratings, which conventionally require a different metrology tool, e.g. critical dimension-scanning electron microscopy (CD-SEM), than is used to measure planar thin films.

One tool that is sometimes used to measure diffracting structures is a scatterometer. Scatterometry is an angle-resolved measurement and characterization of light scattered from a structure. Scatterometry is discussed in detail in U.S. Ser. No. 09/036,557, filed Mar. 6, 1998, now U.S. Pat. No. 6,483,580 B1, which has an International Publication No. WO 99/45340, dated Sep. 10, 1999, and which is incorporated herein by reference.

U.S. Ser. No. 09/036,557 discloses the use of a spectroscopic ellipsometer to measure the diffracting structure. The sampling beam is incident on the sample at an oblique angle. The incident light of the spectroscopic ellipsometer is polarized to provide a beam in the TE mode (S-polarized) when the incidence plane of the beam is perpendicular to the grating of the diffracting structure or to provide a beam in the TM mode (P-polarized) when the incidence plane of the beam is parallel to the grating. Aligning the incident radiation with the grating of the diffracting structure unfortunately is difficult, particularly where the wafer stage is an r-θ stage. With an r-θ stage, the entire metrology apparatus must be rotated to properly align the incident radiation with the grating. U.S. Ser. No. 09/036,557 discloses a dedicated scatterometer instrument that uses a spectroscopic ellipsometer with non-normal incident light and that is used in a scatterometer mode.

In addition, U.S. Ser. No. 09/036,557 teaches that a reference database is generated using optical modeling. The reference database is simplified by measuring the film thickness and optical indices of film underlying the diffracting structure. Thus, prior to ellipsometrically measuring the diffraction grating, a measurement of the underlying film is performed. A broadband ellipsometric measurement is then made at a single polarization orientation, and the reference database is consulted to determine the structure of the diffraction grating. As can be seen, even though the size of the database is reduced by measuring the film thickness and optical indices of the underlying film, this process still requires the generation of a relatively large database. Further, the sample or metrology device must be moved and refocused to measure the underlying film, i.e., without the diffracting structure, and the diffracting structure itself, which is time intensive.

Thus, what is needed is an optical metrology tool to quickly and accurately measure diffraction gratings, as well as other non-diffracting structures, and that may be used with various wafer stages, including X, Y, Z, θ stages, as well as stages capable of r-θ movement only.

SUMMARY

A normal incidence reflectometer uses normally incident broadband radiation to measure one or more parameters of a diffracting structure. A rotatable analyzer/polarizer is used to analyze the diffracted radiation that is reflected off the diffracting structure. Relative rotation of the rotatable analyzer/polarizer with respect to the diffracting structure permits analysis of the diffracted radiation at multiple polarity orientations. The analyzer/polarizer is a single unit, which advantageously reduces cost and simplifies operation. A spectrograph detects the intensity of the spectral components at different polarity orientations. Because the normal incidence reflectometer, in accordance with the present invention, uses normally incident radiation and an analyzer that rotates relative to the diffracting structure, or vice-versa, the orientation of the grating of the diffracting structure does not affect the accuracy of the measurement. Consequently, different types of sample stages, including X, Y, and Z, as well as r-θ type stages may be used. Further, the normal incidence reflectometer advantageously does not require that the polarization orientation of the incident light be aligned with the grating of the diffraction structure.

One aspect of the present invention is directed towards an apparatus for measuring one or more parameters of a diffracting structure on a sample, the apparatus includes a radiation source that emits broadband radiation, a polarizing element that polarizes the radiation, which is then normally incident on the diffracting structure. At least one of the polarizing element and the diffracting structure are rotatable such that a plurality of polarization orientations of the polarizing element with respect to the diffracting structure may be achieved. The light is reflected off the diffracting structure, passes through the polarizing element and received by a spectrograph that detects the intensity of spectral components of said polarized beam at different polarization orientations of the polarizing element with respect to the diffracting structure. Thus, multiple orientations of the polarization of the reflected light may be received by the spectrograph.

Another aspect of the present invention includes an apparatus for measuring one or more parameters of a diffracting structure on a sample, the apparatus includes a radiation source that emits broadband radiation that is normally incident on the diffracting structure, a polarizing element that is in the beam path of the radiation, an r-θ sample stage that holds the sample with the diffracting structure, and a spectrograph that detects the intensity of spectral components of radiation reflected off said diffracting structure. The polarizing element is positioned such that the radiation passes through the polarizing element toward said sample, the radiation is reflected off the diffracting structure on the sample, the reflected radiation passes through the polarizing element, and the polarizing element is rotatable to produce a relative rotation between said polarizing element and said diffracting structure. The spectrograph detects the intensity of spectral components of the reflected radiation after passing through the polarizing element at a plurality of polarization orientations between the polarizing element and the diffracting structure.

Another aspect of the present invention includes a computer system including a computer coupled to the spectrograph and that receives the spectrograph signals, includes computer instructions for analyzing the spectrograph signals and extracting spectral information from the signals. The computer instructions also include instructions for generating an optical model of the diffracting structure, such as through rigorous coupled-wave analysis, calculating the spectral information from the optical model and curve fitting the optical model to the extracted spectral information, while adjusting variable parameters of the diffracting grating, such as height, pitch, sidewall angle, and critical dimension to achieve a best fit. In one embodiment, the computer system includes instructions to perform a non-linear multivariate regression process to adjust the parameters of the optical model.

Another aspect of the present invention is directed towards a method of measuring at least one parameter of a diffracting structure, including directing normally incident radiation at a plurality of wavelengths and at a plurality of polarization orientations at the diffracting structure, the radiation reflecting off and diffracted by the diffracting structure on the sample; analyzing the radiation that is reflected off and diffracted by the diffracting structure to produce an output beam with the same polarization orientations; detecting the intensity of spectral components of the output beam at the plurality of polarization orientations; and using the detected intensities of the spectral components of the output beam to determine at least one parameter of the diffracting structure. The method may also include generating a reference database of at least one parameter related to different diffracting structures for a plurality of wavelengths and the plurality of polarity orientations and comparing the detected intensities of the spectral components to the database to determine at least one parameter of said diffracting structure.

DETAILED DESCRIPTION

Figure 1:
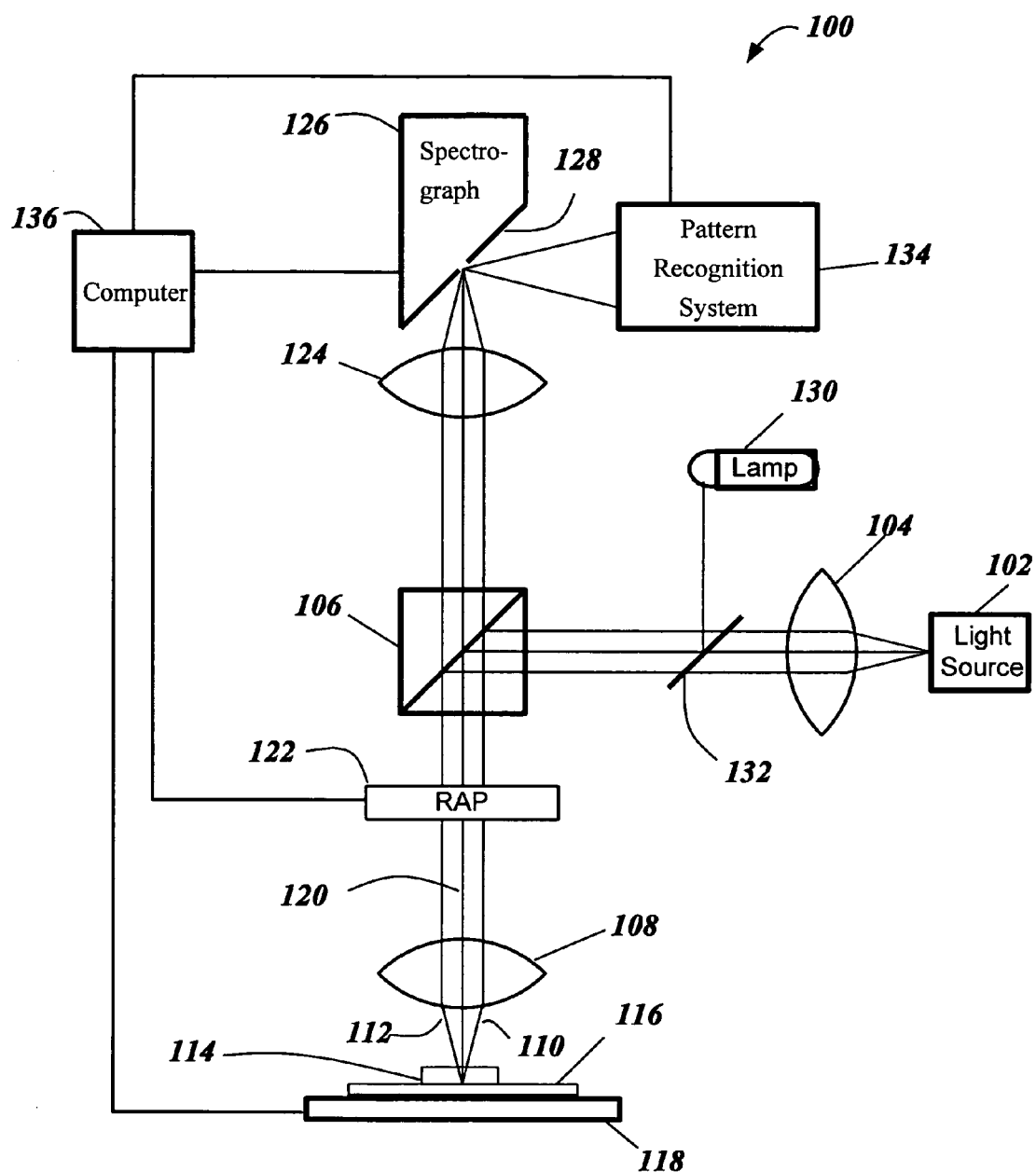
FIG. 1 is a schematic diagram of a normal incidence reflectometer with a rotatable analyzer/polarizer that may be used to measure diffracting structures, in accordance with an embodiment of the present invention.

FIG. 1 is a schematic diagram of a normal incidence reflectometer 100 with a rotatable analyzer/polarizer 122 and that may be used to measure diffracting structures, in accordance with an embodiment of the present invention. The use of a single polarizing element as a rotatable analyzer/polarizer 122, advantageously, permits measurement of diffracting structures with a reduced number of parts. Moreover, normal incidence reflectometer 100 may be used as a reflectometer to measure non-diffracting structures. Thus, normal incidence reflectometer 100 advantageously need not be a dedicated metrology tool that is used to measure only diffraction gratings, but may be used for other reflectometer-type applications as well.

Normal incidence reflectometer 100 includes a broadband light source 102, such as a UV-visible light source with wavelengths, e.g., between 200 nm to 800 nm, that produces unpolarized light. The unpolarized light is collected and collimated by lens 104. Beam splitter 106 directs a portion of the collimated, broadband, unpolarized light beam toward the sample that is held on a movable sample stage 118. The sample may be, e.g., a diffraction grating structure 114 on a patterned silicon wafer 116. It should be understood, of course, that grating structure 114 is typically very small and that its size shown in FIG. 1 is exaggerated for the sake of clarity.

Disposed between the beam splitter 106 and the sample 114 is the rotatable analyzer/polarizer ("RAP") 122. The light reflected by beam splitter 106 toward the sample passes through the RAP 122 and is linearly polarized. The rotation of RAP 122 is controlled by a computer 136 in a manner known to those skilled in the art. In another embodiment, RAP 122 is stationary while computer 136 rotates sample stage 118 so that the grating structure 114 is rotated relative to RAP 122.

The RAP 122 passes only the electric field component of the light that is coincident with the polarization axis of the RAP 122 and thus controls the orientation of the light that is incident on the sample. The RAP 122 may be, e.g., Glan Taylor air-spaced polarizer, a dichroic Poloroid sheet, or any other appropriate linearly polarizing device. The light from RAP 122 is focused by objective 108 so that the light is normally incident on grating structure 114. While marginal rays 110 and 112 are at small angles from the normal ray 120 on the sample, the angles are too small to see any polarization effects that occur in conventional ellipsometers. Because RAP 122 is rotated relative to the diffraction structure 114, i.e., RAP 122 and/or diffraction structure 114 is rotated, the polarization orientation of the incident light need not be aligned with the grating of the diffraction structure 114 prior to the metrology process. Consequently, normal incidence reflectometer 100 may be used, advantageously, with a wafer stage 118 that is capable of any or all of x, y, z, and/or Θ movement, as well as a stage that is capable of r-θ movement only.

Diffracted light from the grating structure 114 is re-collimated by lens 108 and passes through the RAP 122, which linearly polarizes the light. The light has an electric field component that is either parallel (sometimes called TE or S-polarization) or perpendicular (sometimes called TM or P-polarization) to the lines of the grating structure 114. The light that is diffracted from grating structure 114 will have a different electric field component intensities and phase than the light that is incident on the structure 114. The RAP 122 passes only the electric field component of the reflected beam that is coincident with the polarization axis of the RAP 122. Thus, RAP 122 advantageously permits detection of different spectral components of the diffracted light.

The light then passes through the beamsplitter 106. The light is then focused by lens 124 to the entrance slit of a spectrograph 126. In an another embodiment, lens 108 may be replaced with a microscope objective and lens 124 removed. Spectrograph 126 may be a conventional CCD, PDA, or similar type spectrograph that disperses the full spectrum of the polarized light into spectral components across an array of detector pixels. Each pixel corresponds to a different wavelength, and thus the spectrograph 126 generates a spectrograph signal, S(λ), as a function of wavelength λ that is transmitted to computer 136. The signal S(λ) is corrected for electronic background as is well known in the art. Because the RAP 122 is rotated through a discrete set or continuous set of angles, Θ, from 0 to 360 degrees, the signal S(λ) is also a function of angle, S(λ, Θ).

The sample may be viewed and aligned using, e.g., a lamp 130 that produces visible light to provide flood illumination via movable mirror 132. This flood illumination is reflected off mirror 128 to a camera and pattern recognition system 134, which may be coupled to computer 136. The pattern recognition system 134 can provide a measure of orientation of grating structure 114 relative to the RAP 122, if desired, as well as serve as a conventional detector for the sample height. The pattern recognition system 134 provides data to the computer 136, which accordingly adjusts the height of stage 118.

The normal incidence reflectometer 100, in accordance with the present invention, operates in a manner similar to a reflectometer but includes the RAP 122 and uses a relative rotation of the sample, i.e., grating structure 114, and the RAP 122; either RAP 122, sample support 118 or both are rotated. Because components of the normal incidence reflectometer 100, such as beamsplitter 106 and spectrograph 126, have polarization dependent efficiencies, multiple calibrations are performed so that a plurality of orientations of the RAP 122 with respect to the diffraction grating structure 114 are measured relative to some arbitrary machine fiducial. Conventional reflectometers, on the other hand, require only a single calibration and do not use polarizer/analyzer.

Figure 2:
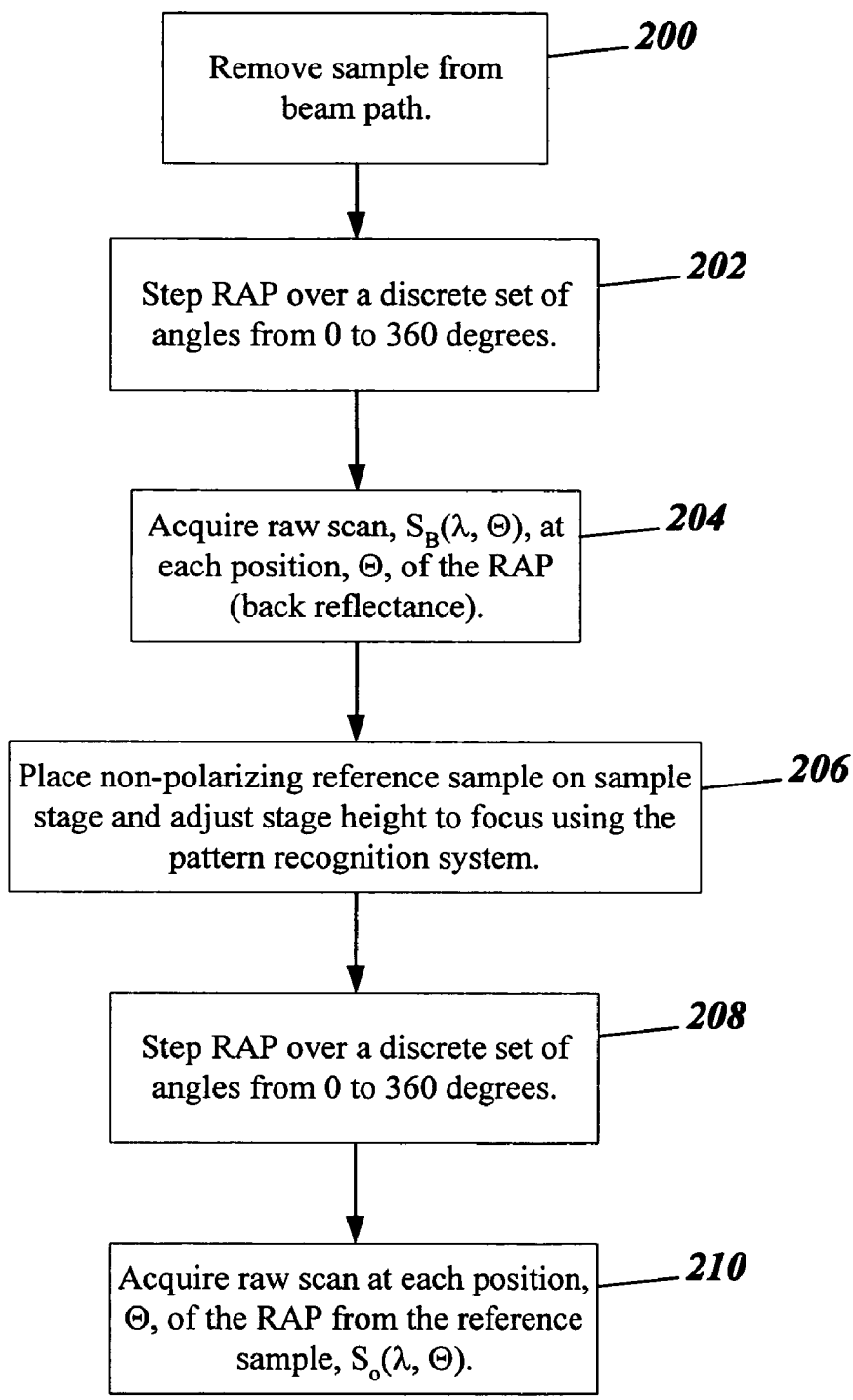
FIG. 2 is a flow chart describing the process of calibrating normal incidence reflectometer.

FIG. 2 is a flow chart describing the process of calibrating normal incidence reflectometer 100. It should be understood that the calibration process does not need to be performed for every measurement, but only periodically, e.g., whenever the alignments of the optical elements have changed. The calibration process includes removing the sample from the beam path so that only light reflected from optical elements reaches spectrograph 126 (step 200). The RAP 122 is stepped over a discrete (or continuous) set of angles e.g., from 0 to 360 degrees or 0 to 180 degrees (step 202). A raw spectrograph scan $S_B(\lambda, \Theta)$, for the back reflectance, is acquired at each position, Θ, of the RAP 122 over the set of angles from 0 to 360 degrees (step 204). The back reflectance scan is used to correct for internal reflections. An integral part of any spectrograph scan is the subtraction of dark counts, i.e., measure with light from the source blocked, to measure and correct for electronic background noise, which is well understood in the art.

A non-polarizing (at normal incidence) reference sample, e.g., bare silicon with a native oxide, is placed on the sample stage and the stage height is adjusted, e.g., using the pattern recognition system 134 (step 206). The RAP 122 is stepped over a discrete (or continuous) set of angles from 0 to 360 degrees (step 208) while a raw scan $S_O(\lambda, \Theta)$ from the reference sample is acquired at each position, Θ, of the RAP 122 (step 210).

Thus, the calibration of normal incidence reflectometer 100 produces the function $S_o(\lambda, \Theta)$. Ideally, the calibrations would be performed for continuous orientations of the RAP 122 with respect to the diffraction grating structure 114, but in practice, this may be done at a discrete set of equally spaced angles, e.g., 1 to 5 degrees apart. The function $S_o(\lambda, \Theta)$ for an angle between two of the equally spaced angles would be calculated by a suitable interpolation scheme, e.g., cubic spline, on a wavelength by wavelength basis.

Figure 3:
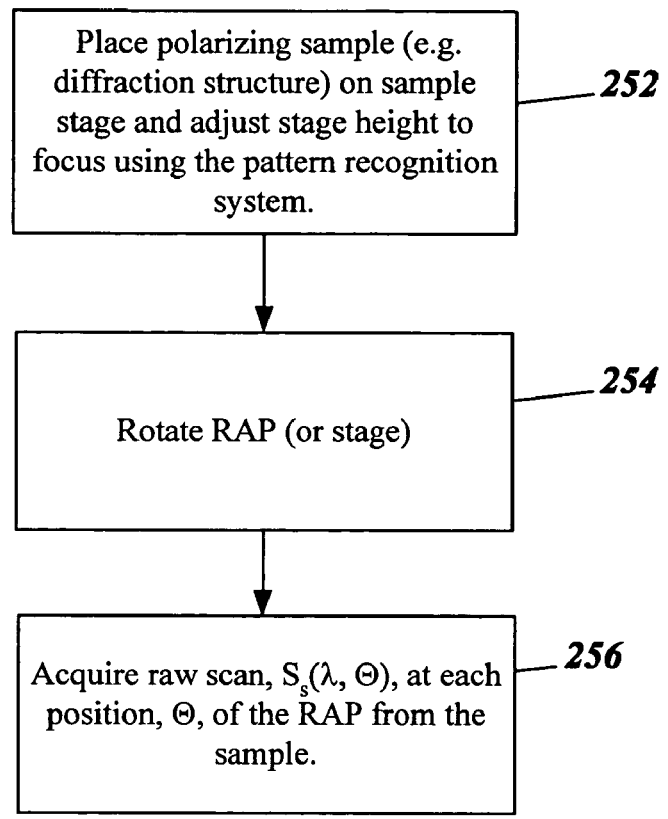
FIG. 3 is a flow chart showing the process of acquiring sample data in accordance with an embodiment of the present invention.

With the normal incidence reflectometer 100 calibrated, the sample data may be acquired. FIG. 3 is a flow chart showing the process of acquiring sample data in accordance with an embodiment of the present invention. The polarizing sample, e.g., wafer 116 with grating structure 114, is placed on the sample stage 118 and the height of the stage 118 is adjusted to focus using, e.g., the pattern recognition system 134 (step 252). The RAP 122 is stepped over the discrete (or continuous) set of angles from 0 to 360 degrees or, alternatively, the stage 118 is rotated, (step 254) and the raw scan $S_S(\lambda, \Theta)$ of the sample is acquired for each position, Θ, of the RAP 122 (step 256). The sample reflectance $R_S(\lambda, \Theta)$ for each position of the RAP 122 is then calculated as follows:

$$R_S(\lambda, \Theta) = \frac{S_S(\lambda, \Theta) - S_B(\lambda, \Theta)}{S_o(\lambda, \Theta) - S_B(\lambda, \Theta)} \cdot R_o(\lambda) \qquad \text{eq. 1}$$

where $R_O(\lambda)$ is the known reflectance of the non-polarizing (at normal incidence) reference sample, e.g., bare silicon with a native oxide from step 206. The reflectance $R_O(\lambda)$ may be determined by measurement or by consulting a library of known reflectances, or calculation from known thicknesses and optical constants of the reference sample. A method of determining absolute reflectance is described in detail in Re. 34,783, reissued Nov. 8, 1994, which is a reissue of U.S. Pat. No. 5,045,704, issued Sep. 3, 1991 to V. Coates and assigned to Nanometrics, Inc., and which is incorporated herein by reference.

With the sample data acquired, the spectral information must be extracted. To do this, it is necessary to analyze the optical system. In the Jones matrix formalism, the electric fields of a plane propagating electromagnetic wave are expressed as a complex valued 2×1 matrix (vector). The effects of polarization altering devices (e.g. beam splitters, diffraction structures, polarizers, etc.) are expressed as 2×2 complex valued transformation vectors. The electric field of the wave exiting the beam splitter 106 towards the spectrograph 126 is given by, $$F(\phi, \Theta) = \begin{pmatrix} t_S & 0 \\ 0 & t_P \end{pmatrix} \cdot R(-\Theta) \cdot \begin{pmatrix} A & 0 \\ 0 & 0 \end{pmatrix} \cdot R(\Theta) \cdot R(-\phi) \cdot \qquad \text{eq. 2}$$
$$\begin{pmatrix} r_{TM} & 0 \\ 0 & r_{TE} \end{pmatrix} \cdot R(\phi) \cdot R(-\Theta) \cdot \begin{pmatrix} A & 0 \\ 0 & 0 \end{pmatrix} \cdot R(\Theta) \begin{pmatrix} r_S & 0 \\ 0 & r_P \end{pmatrix} \cdot \begin{pmatrix} a \\ b \end{pmatrix}$$

where, $r_{TM}$ and $r_{TE}$ are the complex valued reflectivities for light polarized perpendicular and parallel to the lines of the diffraction structure, respectively, and, $r_s$, $r_p$, and $t_s$, $t_p$ are the reflectivity coefficients and transmissivity coefficients, respectively, for the s-polarized or p-polarized states of the electric field vector at the beam splitter. The matrix $$R(\varphi) = \begin{pmatrix} \cos\varphi & -\sin\varphi \\ \sin\varphi & \cos\varphi \end{pmatrix} \qquad \text{eq. 3}$$

is a coordinate rotation by some angle, φ, and the matrix $$\begin{pmatrix} A & 0 \\ 0 & 0 \end{pmatrix} \qquad \text{eq. 4}$$

corresponds to the polarizing element of the RAP 122. Simplifying the above equation yields $$F(\phi, \Theta) = A^2\beta(\Theta) \cdot [r_{TM} \cdot \cos^2(\phi - \Theta) + r_{TE} \cdot \sin^2(\phi - \Theta)] \cdot \begin{pmatrix} t_S \cdot \cos\Theta \\ -t_P \cdot \sin\Theta \end{pmatrix} \quad \text{eq. 5}$$

where $\beta(\Theta) = r_S a \cdot \cos\Theta + r_P b \cdot \sin\Theta$.

The measurable intensity will then be proportional to $$|F(\phi,\Theta)|^2 = A^4 |\beta(\Theta)|^2 \cdot (|t_S \cos\Theta|^2 + |t_P \sin\Theta|^2)$$
$$[|r_{TM}|^2 \cos^4(\phi-\Theta) + |r_{TE}|^2 \sin^4(\phi-\Theta) + (r_{TM} r_{TE}^* + r_{TM}^* r_{TE}) \cos^2(\phi-\Theta) \sin^2(\phi-\Theta)] \quad \text{eq. 6}$$

Writing the reflectivities, $r_{TM}$ and $r_{TE}$ in terms of their amplitudes and phases, the cross term in the above equation becomes $(r_{TM} r_{TE}^* + r_{TM}^* r_{TE}) = 2 \cdot |r_{TM}| \cdot |r_{TE}| \cdot \cos\Delta$ where $\Delta = \phi_{TE} - \phi_{TM}$ is the phase difference between TE and TM reflectivities. In the special case when, $r_{TM} = r_{TE} = r_O$, equation 6 simplifies to $$|F_O(\phi,\Theta)|^2 = A^4 |\beta(\Theta)|^2 \cdot (|t_S \cos\Theta|^2 + |t_P \sin\Theta|^2) \cdot |r_O|^2 \quad \text{eq. 7}$$

Now we have the following relationship where to the left of the equality sign we have known or measurable quantities and on the right side of the equation are the unknowns to be determined.

$$\frac{|F(\phi,\Theta)|^2}{|F_O(\phi,\Theta)|^2} |r_O|^2 = |r_{TM}|^2 \cos^4(\phi-\Theta) + |r_{TE}|^2 \sin^4(\phi-\Theta) + 2 \cdot |r_{TM}| \cdot |r_{TE}| \cdot \cos\Delta \cdot \cos^2(\phi-\Theta) \sin^2(\phi-\Theta) \quad \text{eq. 8}$$

The quantity on the left side is the absolute reflectance of the sample, $R_S(\lambda, \Theta)$, as a function of wavelength $\lambda$ and the angle $\Theta$ of RAP 122 relative to the diffraction grating 114. A method of determining absolute reflectance is described in detail in Re. 34,783, reissued Nov. 8, 1994, which is a reissue of U.S. Pat. No. 5,045,704, issued Sep. 3, 1991 to V. Coates and assigned to Nanometrics, Inc., and which is incorporated herein by reference.

Figure 4:
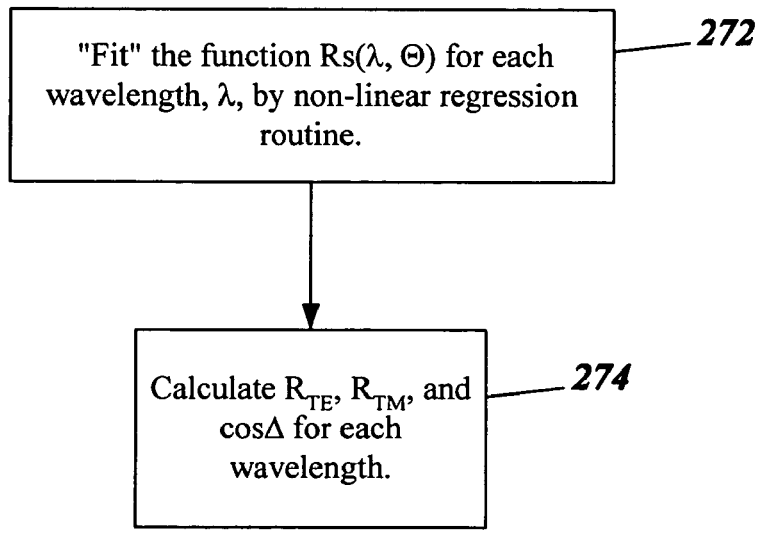
FIG. 4 is a flow chart of the process of extracting spectral information in accordance with the present invention.

FIG. 4 is a flow chart of the process of extracting spectral information. The spectral information is extracted by curve fitting the function $R_S(\lambda, \Theta)$ for each wavelength, $\lambda$, using a non-linear regression analysis, e.g., the Levenberg-Marquardt algorithm, to the following function derived from equation 8.

$$R(\Theta) = A \cdot \cos^4(\phi-\Theta) + B \cdot \sin^4(\phi-\Theta) + C \cdot \cos^2(\phi-\Theta) \cdot \sin^2(\phi-\Theta) \quad \text{eq. 9}$$

where adjustable parameters, i.e., measurables, are $\phi$, A, B, and C, which indicates that the minimum number of RAP 122 orientations needed is four (step 272).

It should be understood that other methods of spectral information extraction may be used, for example, equation 2 may be inverted and the parameters directly calculated. This is advantageous because no iteration is required, but may have somewhat limited application, e.g., may not provide an accurate answer for all functions. In particular, data can be acquired at four equally spaced angles $\delta$, $\delta+\pi/4$, $\delta+\pi/2$, and $\delta+3\pi/4$ over one 180 degree period where $\delta=\phi-\Theta_1$ and $\Theta_1$ is the first RAP 122 angle of acquisition. Make the substitutions $$x = \cos^2(\phi-\Theta); \alpha = A+B-C; \beta = C-2B; \gamma = B \quad \text{eq. 10}$$

into equation 9 to obtain the following system of four equations.

$$R_{S1} = \alpha \cdot x_1^2 + \beta \cdot x_1 + \gamma; \quad \text{eq. 11}$$

$$R_{S2} = \alpha \cdot x_2^2 + \beta \cdot x_2 + \gamma; \quad \text{eq. 12}$$

$$R_{S3} = \alpha \cdot x_3^2 + \beta \cdot x_3 + \gamma; \text{ and} \quad \text{eq. 13}$$

$$R_{S4} = \alpha \cdot x_4^2 + \beta \cdot x_4 + \gamma. \quad \text{eq. 14}$$

Note $x_1$, $x_2$, $x_3$, $x_4$ are all functions of $\delta$ so the four unknowns are $\alpha$, $\beta$, $\gamma$, and $\delta$. The above system can be inverted according to the following equations.

$$\delta = \arctan\left[\frac{R_{S2} - R_{S4}}{R_{S3} - R_{S1}}\right]; \quad \text{eq. 15}$$

$$\alpha = 2 \cdot \left[\frac{R_{S1} + R_{S3} - R_{S2} - R_{S4}}{\cos(4\delta)}\right]; \quad \text{eq. 16}$$

$$\beta = \sqrt{(R_{S1} - R_{S3})^2 + (R_{S2} - R_{S4})^2} - \alpha; \text{ and} \quad \text{eq. 17}$$

$$\gamma = \frac{1}{4} \cdot \left(R_{S1} + R_{S2} + R_{S3} + R_{S4} - \frac{3\alpha}{2} + 2\beta\right). \quad \text{eq. 18}$$

Finally, A, B, and C may be calculated according to:

$$A = \alpha + \beta + \gamma; B = \gamma; C = \beta + 2\gamma. \quad \text{eq. 19}$$

As indicated in FIG. 4, the $R_{TE}$, $R_{TM}$ and $\cos\Delta$ are then calculated (step 274), as follows:

$$R_{TE} = A; R_{TM} = B; \cos\Delta = \frac{C}{2\sqrt{AB}}; \text{ or} \quad \text{eq. 20}$$

$$R_{TE} = B; R_{TM} = A; \cos\Delta = \frac{C}{2\sqrt{AB}}. \quad \text{eq. 21}$$

Because of the symmetry of equation 2, it is not known which equation of equations 20 and 21 is correct. The correct equation is determined using knowledge of the orientation of the diffracting structure taken from the manufacturing process and knowledge of the approximate orientation of the RAP 122, e.g., as determined by pattern recognition system 134. The TM and TE orientations are always 90 degrees apart, and thus, the polarization angle of the RAP 122 does not need to be known with great accuracy, ±20 degrees should be adequate. There are two analyzer angles, $\Theta_{TE}$ and $\Theta_{TE}+\pi$ or when the analyzer will pass only the TE component and two analyzer angles, $\Theta_{TE}\pm\pi/2$ when the analyzer will pass only the TM component. Because the electric field of the reflected beam can be written as a superposition of TE and TM components relative to the diffraction grating, the reflected intensity, $R_S(\lambda)$, will have oscillatory variation with $\Theta$ reaching extrema at $\Theta_{TE}$, $\Theta_{TE}+\pi/2$. The absolute reflectances for TE and TM components are labeled $R_{TE}(\lambda)$ and $R_{TM}(\lambda)$, respectively. Whether a particular extrema corresponds to TE or TM light can be determined from the knowledge of the sample orientation and the pattern recognition system. The approximate orientation of any polarizing device can be measured or approximated by anyone skilled in the art.

Actual measurements can be made in either an absolute fashion where the RAP 122 is driven to the TM and TE positions by computer 136 or in a relative fashion where the analyzer is rotated continuously.

Another method that can be used to extract spectral information is performed by, first, loading the wafer on the sample stage with the diffraction structure lines approximately parallel to the RAP 122 transmission axis. Then, measure $R_S(\Theta)$ for a plurality of values of $\Theta$, e.g., 5 to 20 values, varying from −20 degrees to +20 degrees. Plot $R_S(\Theta)$ and fit this function to a parabola, identifying the extremum as $\Theta_{TE}$. Rotate the RAP 122 to $\Theta=\Theta_{TE}$, and measure $R_S$. This would be identified as $R_{TE}$. Finally, rotate the RAP 122 to $\Theta=\Theta_{TE}\pm\pi/4$ and measure $R_S$. This would be identified as $R_{TM}$.

Advantageously, because normal incidence reflectometer 100 includes a rotating element, i.e., the RAP 122 and/or sample stage 118, and operates at normal incidence, the orientation of the grating structure 114 does not affect the accuracy of the measurement. The optics are always aligned to the structure. This is of particular advantage when coupled with an r-θ sample stage.

The reflectances $R_{TE}(\lambda)$ and $R_{TM}(\lambda)$ from the polarizing diffraction grating can be used to deduce information about the grating such as pitch, linewidth, and lineshape via exact modeling of $R_{TE}(\lambda)$, $R_{TM}(\lambda)$, and cos $\Delta(\lambda)$ spectra using, e.g., rigorous coupled wave analysis ("RCWA"). For more information regarding RCWA, see M. G. Moharam and T. K. Gaylord, "Rigorous coupled-wave analysis of planar grating diffraction", J. Opt. Soc. Am., Vol. 71, No. 7, pp. 811-818, (1983); M. Moharam et al., "Stable implementation of the rigorous coupled wave analysis for surface-relief gratings: enhanced transmittance matrix approach," J. Opt. Soc. Am. A., Vol. 12, No. 5, pp. 1077-1086 (1995); T. Gaylord et al., "Analysis and Applications of Optical Diffraction by Gratings," Proceedings of the IEEE, Vol. 73, No. 5, pp. 894-937 (1985), N. Chateau and J. P. Hugonin, "Algorithm for the rigorous coupled-wave analysis of grating diffraction," J. Opt. Soc. Am. A, Vol. 11, No. 4, April 1994, pp. 1321-1331; and M. G. Gaylord et. al., "Formulation for stable and efficient implementation of the rigorous coupled-wave analysis of binary grating," J. Opt. Soc. Am. A, Vol. 12, No. 5, May 1995, pp. 1068-1076, which are incorporated herein by reference.

A difficulty with RCWA analysis has been the very large amount of computation that must be done to accurately simulate the optical response of a grating structure. In particular, the reflected TM light calculation converges very slowly. Most solutions have been to build large libraries of response curves offline and search the library for a best match at the time of measurement. The present invention, advantageously, allows for the separation of the TE and TM components. A library can be searched, matching both TE and TM components for a rough estimation of the diffracting structure and then relatively fast, real time iteration on normal incidence TE light can be used to refine the measurement. The Levenberg-Marquardt non-linear multivariate regression process is used to adjust the parameters in the RCWA model such that the reflectance spectrum predicted by the model matches a given measured spectrum as closely as possible. The Levenberg-Marquardt non-linear multivariate regression is discussed in "Numerical Recipes: The Art of Scientific Computing," by W. Press, et al., Cambridge University Press, 1986, Section 14.4, pp. 521-528.

Figure 5:
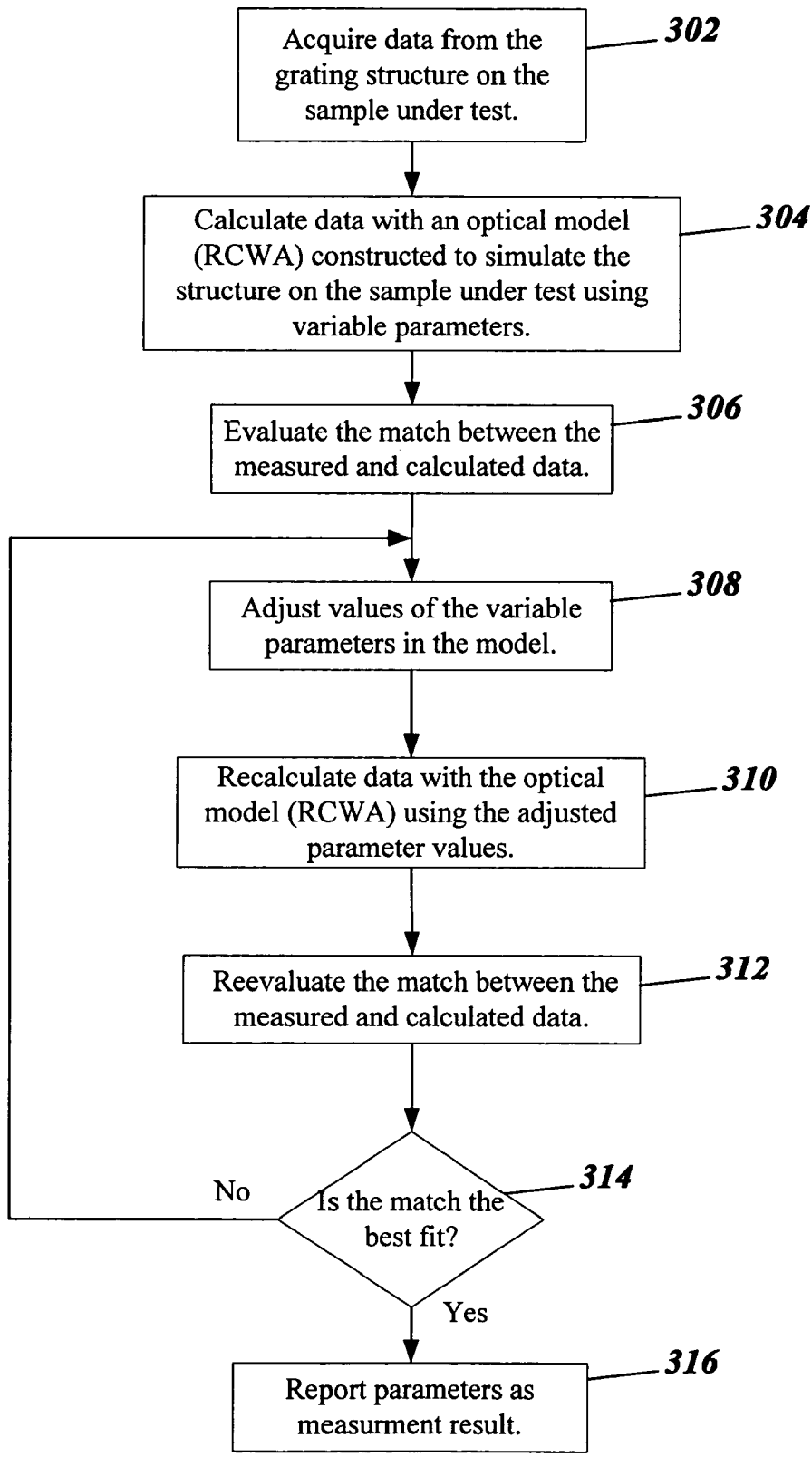
FIG. 5 is a flow chart of the process of data analysis in accordance with the present invention.

FIG. 5 is a flow chart of the process of data analysis in accordance with the present invention. The data analysis may be performed, e.g., by computer 136, which executes a computer program with appropriate computer instructions. The spectral data, i.e., $R_{TM}(\lambda)$, $R_{TE}(\lambda)$, and cos $\Delta$, is acquired as discussed above in reference to FIGS. 2, 3, and 4 (step 302). An optical model is constructed to simulate the structure on the sample under test and the spectral data is calculated (step 304). The optical model is constructed using, e.g., the RCWA model, with variable parameters, such as layer thickness, grating linewidth, sidewall angle of the grating, and optical constants of the materials in the model.

Computer 136, or another computer that is in communication with computer 136, executes a computer program with computer instructions to calculate the model spectrum using the RCWA model as described by the following pseudo-code. Calculations of the model spectrum are performed for each wavelength. Inputs to the calculation are the optical constants and thickness of each layer in the model, and all grating parameters for any grating layer in the model. Note that "I" designates the identity matrix, and that all matrices and vectors referred to below are defined in Moharam, Pommet, Grann, and Gaylord, J. Opt. Soc. Am. A, vol. 12, No. 5, 5/1995, pp. 1077-1086, which is incorporated herein by reference. Unless otherwise noted all matrices are of dimension N by N, where N=2*number of diffracted orders +1.

```
Beginning:
  Calculate initial matrix f (equal to the identity matrix);
  Calculate initial matrix g (function of substrate parameters only);
  Loop over layers in the model, starting at the bottom layer (next to
    substrate);
  Calculate matrix E of Fourier coefficients for the dielectric function;
  Calculate matrix P of Fourier coefficients for the inverse of the dielectric
    function;
  Invert E and store in Einv;
  Invert P and store in Pinv;
  Calculate x-component of the wavevector for each diffracted order, place
    on diagonal of the diagonal matrix Kx;
  Construct eigenproblem matrix from the above three results:
    If TE mode, eigenproblem matrix is:
      A=Kx*Kx−I;
    Else if TM mode, eigenproblem matrix is:
      A=Pinv*(Kx*Einv*Kx − I)
    End if
  Solve for eigenvalues and eigenvectors of matrix A;
  Store eigenvalues on diagonal of (diagonal) matrix Q.
  Store eigenvectors in columns of matrix W;
  If TE mode;
    Calculate matrix V=W*Q;
  Else if TM mode;
    Calculate matrix V=P*W*Q;
  End if
  Calculate diagonal matrix X − diagonal elements are exp(−Qii*thickness)
  Construct temporary 2N*2N matrix as follows:
    Upper left block is −W;
    Upper right block is f;
    Lower left block is V;
    Lower right block is g;
  Invert this temporary matrix;
  Let Temp00 be the upper left block of the inverted temporary matrix;
  Let Temp01 be the upper right block of the inverted temporary matrix;
  Calculate matrix a=Temp00*W*X+Temp01*V*X;
  Calculate new f matrix as f=W*(I+X*a);
  Calculate new g matrix as g=V*(I−X*a);
  Repeat for Next Layer
  Comment: Construct and solve final system of linear equations to get
```

-continued
```
Reflected fields for each diffracted order;
Calculate diagonal matrix ZI, with diagonal elements equal to the z
  component of the wavevector of each diffracted order in the ambient.
Calculate the Coefficient matrix alpha=g*f¹+j*ZI;
Construct vector beta, where
  If I= # of harmonics
    Beta[I]=j-(g*f¹)_{I,I}
  Else
    Beta[I]=(g*f¹)_{I,NumHarmonics}
  End if
Solve system of linear equations defined by alpha and beta;
Solution of this system yields the complex amplitudes of the reflected
  orders;
Calculate the reflectance of the zeroth diffracted order as the square of
  the Magnitude of the complex amplitude of the zeroth reflected order;
End;
```

As shown in FIG. 5, once the data from the optical model is calculated, the match between the measured data and the calculated data is evaluated (step 306). The evaluation of the match may be performed using the Mean-Squared Error (MSE) between the measured and calculated data. If the measured data points are denoted as $y_m(\lambda_I)$ and the calculated data points are denoted as $y_c(\lambda_I)$, then the MSE is given by:

$$MSE = \sum \frac{(y_m(\lambda_I) - y_c(\lambda_I))^2}{N - M} \qquad \text{eq. 22}$$

Where N is the total number of data points and M is the total number of variable parameters in the model. Note that if the measured and calculated data are identical, the MSE value is zero and that the smaller the value of MSE the better the match between the measured and calculated data.

Assuming the MSE value is not zero, the values of the variable parameters in the optical model are appropriately adjusted (step 308), for example, using the Levenberg-Marquardt algorithm, and the optical data is recalculated using the optical model and the adjusted parameter values (step 310). The match between the measured and calculated data is then reevaluated (step 312) to see if the new MSE is less than the previous value. If so, the new parameter values have improved the fit between the measured and calculated data. A decision is made whether a best fit has been derived (step 314), which is determined when adjusting the values in the model does not reduce the value of the MSE any further. Thus, if a best fit has not been achieved, i.e., the fit is still improving (or is worse), the process goes back to step 308, where the values of the variable parameters are appropriately adjusted. If the best fit is achieved, then the variable parameters are reported as the measurement result (step 316).

Computer 136, or another computer that is in communication with computer 136, executes a computer program with computer instructions to perform the process of FIG. 5, as described by the following pseudo-code. It should be understood, that part of the process of FIG. 5 includes the calculation of the model spectrum using the RCWA model, discussed above.

```
Load measured spectrum into Rmeas( );
Load measured wavelengths into Wvls( );
Set initial values of all model parameters;
Set initial value of Marquardt parameter alpha=0.001;
```

-continued
```
Calculate initial spectrum from the model, store in Rcalc( );
Calculate initial MSE value;
Beginning of Main Loop:
  For each variable parameter in the model:
    Add small increment to the variable parameter;
    Recalculate the spectrum from the model with the incremented
      parameter;
    Calculate array of derivatives of MSE with respect to the variable
      parameter from Newton's approximation at each wavelength –
      df/dx= (f(x+δ)-f(x))/δ;
    Restore variable parameter to its original value;
  End of loop on variable parameters;
  Calculate Hessian matrix from calculated derivative arrays and the
  Marquardt parameter;
  Calculate Gradient vector from calculated derivative arrays;
  Solve system of linear equations defined by Hessian matrix and Gradient
    vector;
  Add solution to the vector of variable parameters;
  Recalculate the spectrum from the model using these new parameter
  values;
  Calculate the MSE for this new spectrum;
  If the new MSE is less than the previous MSE, retain these values,
  divide
    the Marquardt parameter by 10, and go back to the beginning of the
    main loop and repeat. If convergence criteria have been reached go to
    the end. Convergence criteria are change in MSE less than some small
    value (10⁻¹⁰, for example) or the maximum number of iterations
    has been reached.
  Else the new MSE is larger than the previous MSE;
    Restore variable parameter values back to what they were at the
      beginning of the iteration.
    Multiply the Marquardt parameter by 10;
    If the maximum number of iterations is exceeded, go to the end.
    Go to the beginning of the main loop for the next iteration.
  End if;
End of Main Loop;
End:
```

Although the invention has been described with reference to particular embodiments, the description is only an example of the invention's application and should not be taken as a limitation. In particular, although the above description is directed mostly to a system that uses a RCWA analysis coupled with real-time non-linear regression analysis, e.g., the Levenberg-Marquardt analysis, to measuring a diffraction grating structure, other methods of analysis may be used if desired, such as RCWA analysis, an initial reference database search followed by real-time non-linear regression analysis, e.g., the Levenberg-Marquardt analysis. Various other adaptations and combinations of features of the embodiments disclosed are within the scope of the invention as defined by the following claims.

What is claimed is:

1. An apparatus for measuring at least one of height, pitch, sidewall angle, and linewidth of a diffracting structure on a sample, said apparatus comprising:
   a metrology device that measures the reflectance of said diffracting structure and at least one underlying layer on said sample at approximately normal incidence, the metrology device comprising:
      a broadband radiation source that produces radiation with a plurality of wavelengths;
      a polarizing element, said radiation passing through said polarizing element toward said sample, said radiation being approximately normally incident on and diffracted by said diffracting structure and the at least one underlying layer on said sample, a zeroth order diffracted radiation passing through said polarizing element;
      a detector that measures the reflectance of the zeroth order diffracted radiation;

and a computer system for analyzing said diffraction to determine said at least one of height, pitch, sidewall angle, and linewidth of said diffracting structure on said sample, said computer system comprising:
- at least one computer coupled to said metrology device; and
- a computer program executed by said at least one computer, wherein said computer program includes instructions for:
  - extracting spectral information from the measured reflectance of the zeroth order diffracted radiation;
  - constructing an optical model simulating said diffracting structure using at least one variable parameter of height, pitch, sidewall angle, and linewidth and a variable parameter of the at least one underlying layer;
  - calculating spectral information for said optical model; and
  - curve fitting said calculated spectral information to said extracted spectral information to determine said at least one of height, pitch, sidewall angle, and linewidth of said diffracting structure and the variable parameter of the at least one underlying layer on said sample;
  - wherein constructing an optical model, calculating spectral information for said optical model, and curve fitting are performed in real-time.

2. The apparatus of claim 1, wherein said metrology device measures the reflectance at a plurality of wavelengths and a plurality of orientations between the diffracting structure and the polarizing element, wherein said computer instructions for extracting spectral information from the measured reflectance of the zeroth order diffracted radiation comprise computer instructions for:
curve fitting said measured reflectance for said plurality of wavelengths and said plurality of orientations with:

$$R(\Theta)=A\cdot\cos^4(\phi-\Theta)+B\cdot\sin^4(\phi-\Theta)+C\cdot\cos^2(\phi-\Theta)\cdot\sin^2(\phi-\Theta)$$

where $R(\Theta)$ is the measured reflectance at one wavelengths, $\Theta$ is the polarization orientation of said polarizing element with respect to said diffracting structure, and $\phi$, A, B, and C are measurable to obtain said spectral information.

3. The apparatus of claim 1, wherein said metrology device measures the reflectance at a plurality of wavelengths and a plurality of polarization orientations, wherein said computer instructions for extracting spectral information from the measured reflectance of the zeroth order diffracted radiation comprise computer instructions for directly calculating said spectral information from said measured reflectance.

4. The apparatus of claim 1, wherein said computer instructions for curve fitting comprise computer instructions for:
- comparing said extracted spectral information and said spectral information for said optical model;
- adjusting said at least one variable parameter of said optical model;
- recalculating spectral information for said optical model;
- comparing said extracted spectral information and said recalculated spectral information for said optical model; and
- repeatedly adjusting said at least one variable, recalculating spectral information for said optical model, and comparing said extracted spectral information and said recalculated spectral information for said optical model until an acceptable fit is achieved.

5. The apparatus of claim 1, wherein said computer instructions for constructing an optical model and calculating spectral information for said optical model comprise computer instructions for using rigorous coupled-wave analysis.

6. The apparatus of claim 1, wherein said computer instructions further comprise searching a library using the extracted spectral information to determine an estimate of at least one of height, pitch, sidewall angle, and linewidth of said diffracting structure on said sample prior to constructing an optical model, calculating spectral information for said optical model, and curve fitting.

7. The apparatus of claim 6, wherein calculating spectral information for said optical model, and curve fitting is performed using a TE component of light.

8. A method of determining one or more of height, pitch, sidewall angle, and linewidth parameters of a diffracting structure on a sample, said method comprising:
- producing broadband radiation;
- directing said broadband radiation through a polarizing element towards said diffracting structure and at least one underlying layer at approximately normal incidence, said broadband radiation is diffracted by said diffracting structure and the at least one underlying layer to produce at least a zeroth order;
- analyzing the diffracted radiation by passing the zeroth order through said polarizing element to produce a diffraction signal;
- extracting spectral information from said diffraction signal;
- constructing an optical model simulating said diffracting structure using one or more of variable height, pitch, sidewall angle, and linewidth parameters and a variable parameter of the at least one underlying layer;
- calculating spectral information from said optical model;
- curve fitting said extracted spectral information and said calculated spectral information and adjusting said one or more of variable height, pitch, sidewall angle, and linewidth parameters and the variable parameter of the at least one underlying layer to determine said one or more of height, pitch, sidewall angle, and linewidth parameters of said diffracting structure and the variable parameter of the at least one underlying layer on said sample;
- wherein constructing an optical model, calculating spectral information for said optical model, and curve fitting are performed in real-time;
- reporting the determined said one or more of height, pitch, sidewall angle, and linewidth parameters of said diffracting structure on said sample.

9. The method of claim 8, wherein curve fitting comprises:
- comparing said extracted spectral information and said spectral information for said optical model;
- adjusting said one or more of variable height, pitch, sidewall angle, and linewidth parameters and the variable parameter of the at least one underlying layer of said optical model;
- recalculating spectral information for said optical model;
- comparing said extracted spectral information and said recalculated spectral information for said optical model; and
- repeatedly adjusting said one or more of variable height, pitch, sidewall angle, and linewidth parameters and the variable parameter of the at least one underlying layer, recalculating spectral information for said optical model, and comparing said extracted spectral information and said recalculated spectral information for said optical model until an acceptable fit is achieved.

10. The method of claim 8, wherein constructing an optical model and calculating spectral information for said optical model comprises using rigorous coupled-wave analysis.

11. The method of claim 8, further comprising searching a library using the extracted spectral information to determine a rough estimation of at least one of height, pitch, sidewall angle, and linewidth of said diffracting structure on said sample prior to constructing an optical model, calculating spectral information for said optical model, and curve fitting.

12. The method of claim 11, wherein calculating spectral information for said optical model, and curve fitting is performed using a TE component of light.

13. A method of determining one or more of height, pitch, sidewall angle, and linewidth parameters of a diffracting structure on a sample, said method comprising:
producing broadband radiation;
directing said broadband radiation through a polarizing element towards said diffracting structure and at least one underlying layer at approximately normal incidence, said broadband radiation diffracting off said diffracting structure and the at least one underlying layer at a zeroth order;
analyzing the diffracted radiation by passing the zeroth order through said polarizing element to produce a diffraction signal;
extracting spectral information from said diffraction signal;
performing a real-time mathematical modeling analysis using non-linear regression with said extracted spectral information to determine a parameter of the at least one underlying layer while determining said one or more of height, pitch, sidewall angle, and linewidth parameters of said diffracting structure on said sample; and
reporting the determined said one or more of height, pitch, sidewall angle, and linewidth parameters of said diffracting structure on said sample.

14. The method of claim 13, further comprising searching a library using the extracted spectral information to determine a rough estimation of at least one of height, pitch, sidewall angle, and linewidth of said diffracting structure on said sample prior to performing the real-time mathematical modeling analysis.

15. The method of claim 14, wherein performing the real-time mathematical modeling analysis uses only the TE component of light.

16. The method of claim 13, wherein the real-time mathematical modeling analysis is rigorous coupled-wave analysis.

17. A method of determining at least one parameter of a diffracting structure on a sample, said method comprising:
generating polarized broadband light that is incident on a diffracting structure at approximately normal incidence;
analyzing the zeroth order diffracted light from the diffraction grating at a plurality of orientations between the analyzer and the diffraction grating;
generating a reflectance measurement for a plurality of wavelengths using the analyzed zeroth order diffracted light from the diffraction grating at a plurality of orientations to derive measured spectral information; and
searching a library to match the measured spectral information to determine the at least one parameter of the diffracting structure;
reporting the at least one parameter of the diffracting structure.

18. The method of claim 17, wherein searching a library to match the measured spectral information determines an estimate of the at least one parameter of the diffracting structure, the method further comprising improving the determination of the at least one parameter of the diffracting structure using the information derived from searching the library.

19. The method of claim 18, wherein improving the determination of the at least one parameter of the diffracting structure using the information derived from searching the library comprises:
performing a real-time mathematical modeling analysis using non-linear regression with the measured spectral information to increase the accuracy of the determination of the at least one parameter of the diffracting structure.

20. The method of claim 19, wherein performing the real-time mathematical modeling analysis uses only the TE component of light.

21. The method of claim 17, wherein analyzing the zeroth order diffracted light comprises passing the zeroth order diffracted light through a polarizer and detecting the intensity with respect to wavelength.

22. The method of claim 17, wherein generating a reflectance measurement for a plurality of wavelengths using the analyzed zeroth order diffracted light from the diffraction grating at a plurality of orientations comprises
curve fitting the reflectance measurement for said plurality of wavelengths and said plurality of orientations with:

$$R(\Theta) = A \cdot \cos^4(\phi - \Theta) + B \cdot \sin^4(\phi - \Theta) + C \cdot \cos^2(\phi - \Theta) \cdot \sin^2(\phi - \Theta)$$

where $R(\Theta)$ is the reflectance measurement at one wavelengths, $\Theta$ is the polarization orientation of said polarizing element with respect to said diffracting structure, and $\phi$, A, B, and C are measurable to obtain said spectral information.

23. The method of claim 17, wherein searching a library to match the measured spectral information is performed using both TE and TM components of light.

24. A method comprising:
generating polarized broadband light that is approximately normally incident on a diffracting structure and at least one underlying layer on a sample;
analyzing the zeroth order diffracted light from the diffraction grating and the at least one underlying layer;
detecting the intensity of the analyzed zeroth order diffracted light; and
determining a parameter of the at least one underlying layer while determining at least one of height, pitch, sidewall angle, and linewidth of the diffracting structure on a sample by using the detected intensity of the analyzed zeroth order diffracted light, searching a library and generating spectral information in accordance with:

$$R(\Theta) = A \cdot \cos^4(\phi - \Theta) + B \cdot \sin^4(\phi - \Theta) + C \cdot \cos^2(\phi - \Theta) \cdot \sin^2(\phi - \Theta)$$

where $R(\Theta)$ is the reflectance measurement at one wavelengths, $\Theta$ is the polarization orientation of said polarizing element with respect to said diffracting structure, and $\phi$, A, B, and C are measurable to obtain said spectral information;
reporting the determined at least one of height, pitch, sidewall angle, and linewidth of the diffracting structure on a sample.

* * * * *